United States Patent [19]

Nowak et al.

[11] 4,046,832

[45] Sept. 6, 1977

[54] CATALYTIC PROCESS FOR THE PREPARATION OF BUTENES FROM PROPYLENE

[75] Inventors: Edward N. Nowak, Uniontown; Kenneth J. Frech, Tallmadge, both of Ohio

[73] Assignee: The Goodyear Tire & Rubber Company, Akron, Ohio

[21] Appl. No.: 623,879

[22] Filed: Oct. 20, 1975

Related U.S. Application Data

[63] Continuation-in-part of Ser. No. 496,670, Aug. 12, 1974, abandoned.

[51] Int. Cl.² .................. C07C 3/62; B01J 23/22; B01J 23/30
[52] U.S. Cl. .................. 260/683 D; 252/430; 252/456; 252/467
[58] Field of Search .................. 252/430, 456, 467; 260/683 D

[56] References Cited

U.S. PATENT DOCUMENTS

| 2,849,383 | 8/1958 | Hirschler et al. | 252/456 |
|---|---|---|---|
| 3,526,601 | 9/1970 | Fotis, Jr. et al. | 252/430 |
| 3,586,731 | 6/1971 | Heckelsberg | 260/683 D |
| 3,639,381 | 2/1972 | Craven | 252/430 X |
| 3,705,886 | 12/1974 | Kashiwa et al. | 252/430 X |
| 3,715,410 | 2/1973 | Ray et al. | 260/683 D X |
| 3,786,112 | 1/1974 | Reusser et al. | 260/683 D |
| 3,883,606 | 5/1975 | Banks | 260/683 D X |
| 3,940,346 | 2/1976 | Zuech | 260/683 D X |
| 3,981,940 | 9/1976 | Zuech | 260/683 D |

Primary Examiner—Daniel E. Wyman
Assistant Examiner—Thomas A. Waltz
Attorney, Agent, or Firm—F. W. Brunner; J. Y. Clowney

[57] ABSTRACT

There is disclosed a process for the preparation of butenes from propylene using a catalyst comprising from 1 to 15 percent by weight of vanadium oxide — $V_2O_5$ and from 0.1 to 5 percent by weight of tungsten oxide — $WO_3$ impregnated on a support which has a surface area of 10 to 400 square meters per gram which catalyst has been activated by contact with from 0.1 to 10 moles of a trialkylaluminum compound per mole of $V_2O_5$.

5 Claims, No Drawings

CATALYTIC PROCESS FOR THE PREPARATION OF BUTENES FROM PROPYLENE

This application is a continuation-in-part of a Ser. No. 496,670, filed Aug. 12, 1974, now abandoned. This application is directed to a process whereby butenes are prepared from propylene. The process utilizes as a catalyst a mixture of vanadium oxide and tungsten oxide on a suitable support, said catalyst being activated by a trialkylaluminum prior to use.

The catalysts useful in this invention have been found to promote the olefin metathesis process. Olefin metathesis or olefin disproportionation is a reaction in which a unique bond reorganization takes place whereby material possessing carbon to carbon double bonds undergo a redistribution of constituents as depicted in the following equation:

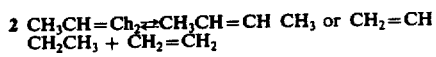

$$2\ CH_3CH=CH_2 \rightleftarrows CH_3CH=CH\ CH_3\ \text{or}\ CH_2=CH\ CH_2CH_3 + CH_2=CH_2$$

Thus, butenes are prepared from propylene.

The catalyst useful in this invention comprises a catalyst comprising a mixture of vanadium oxide ($V_2O_5$) and tungsten oxide ($WO_3$) on a suitable support, said metal oxides being activated by small amounts of trialkylaluminums.

As has been indicated this invention is a process whereby butenes are prepared from a propylene feedstock. The temperature at which the propylene is passed into the reactor and over the catalyst may range broadly from about 20° C. to about 450° C., with 50° C. to 300° C. being more preferred, and from about 100° C. to about 200° C. being most preferred. The rate at which the propylene is fed to the reactor and passed over the catalyst may vary broadly and is reported as gaseous hour space velocity (GHSV) and is in terms of units of volume of propylene as a gas/volume of reactor space/per hour. The GHSV may vary broadly from 10 to 1000 with from 50 to 500 being more preferred and from 100 to 300 being most preferred.

The catalyst is prepared by impregnating $V_2O_5$ and $WO_3$ onto and into a suitable support. This is usually done by using a water soluble or a solvent soluble salt of vanadium and tungsten. These soluble salts are dissolved in a suitable liquid and the salt solution absorbed into and onto the support and then calcined to form the oxides of the vanadium and tungsten, and the subsequent activation with small amounts of trialkylaluminums.

For instance, the catalyst of this invention may be prepared by the impregnation of suitable high area surface supports with aqueous or solvent soluble salts of vanadium in amounts calculated to give a final catalyst containing the desired percentage of $V_2O_5$. The support material containing the vanadium salt is dried, then calcined by heating it to temperatures of about 300° C. to about 900° C. while blowing air or other oxidants over the catalyst to convert the vanadium salts to vanadium oxide, $V_2O_5$. The tungsten oxide portion of the catalyst may be put on the support in the same manner by using aqueous or solvent soluble salts of tungsten in the required amounts calculated to give the desired amount of $WO_3$ in the final catalyst and is dried and calcined under the same conditions to cause the tungsten salts to be converted to tungsten oxide, $WO_3$. The calcination step requires from about 5 minutes to about 3 hours. Those skilled in the art will be able to determine the time required to convert the vanadium and tungsten salts to their oxides. After this treatment, the catalyst is activated by contacting the catalyst with a solvent solution of the trialkylaluminum. After the mixed vanadium oxide/tungsten oxide catalyst has been in contact with the aluminum trialkyl for sufficient time to activate it, the solution of aluminum trialkyl is removed and all excess washed away with fresh solvent. At this time, the catalyst is suitable to use to convert propylene into butenes. This process will be further understood by reference to examples set forth elsewhere in this application.

The vanadium oxide portion of the catalyst may be added to the support material by using various water soluble vanadium salts such as ammonium metavanadate, vanadyl sulfate, vanadium pentoxide in basic solution, or in a hydrocarbon solvent as $VCl_4$, $VOCl_3$ and other soluble vanadium salts. In aqueous solution, $NH_4VO_3$ is additionally solubilized by the addition of oxalic acid. Likewise, the tungsten oxide portion of the catalyst may be added to the support by using various aqueous salts of tungsten such as ammonium metatungstate, sodium metatungstate, $W(OH)_4$ in HCl or in hydrocarbon solvent as $WCl_6$, $WCl_4$, $WOCl_4$ and other soluble tungsten salts.

The supports useful in the practice of this invention are alumina, silica, thoria, zirconia, oxides of titanium or magnesium, and mixtures thereof. These supports are preferred to have a surface area of at least about 10 to about 400 square meters per gram. Alumina and silica are preferred.

The trialkylaluminums useful to activate the catalyst of this invention are represented by aluminum trimethyl, aluminum triethyl, aluminum triisobutyl and other aluminum trialkyls wherein the alkyl groups contain from about 1 to about 12 carbon atoms.

The order in which the two metal oxides are impregnated on or in the catalyst support is not critical. One may impregnate the support with an aqueous solution of a vanadium salt, for instance, ammonium metavanadate, dry and re-impregnate the support material with an aqueous solution of a tungsten salt, for instance, ammonium metatungstate, again dry the support and calcine to convert the tungsten and vanadium salts to their oxides. On the other hand, the reverse order of adding the vanadium and tungsten salts may be employed. Still another method would be to impregnate the support with aqueous $NH_4VO_3$, dry, calcine and impregnate with $(NH_4)_2W_2O_{13}\cdot 8H_2O$, dry and calcine, likewise the reverse order may be employed. Still another method of preparation would be to put the tungsten and vanadium in and on the support as a solution in an organic solvent of $WCl_6$ and $VCl_4$, for instance, oxidize at moderate temperatures and then calcine at temperatures of at least 300° C. In other words, the order in which the salts of vanadium and tungsten are placed on the support is not critical to the preparation of the catalyst.

It is necessary, however, to activate the catalyst with the trialkylaluminums, which step takes place after the vanadium and tungsten salts are converted to oxides.

The amount of vanadium oxide employed in the catalyst of this invention, calculated as $V_2O_5$, should range from about 1 to about 15 percent by weight of the support with from about 3 to about 10 percent being more preferred and about 4 to about 6 percent being even more preferred.

The amount of tungsten oxide employed in the catalyst of this invention, calculated as $WO_3$, should range from about 0.1 to about 5 percent by weight of the support, with from about 0.1 to about 3 percent being more preferred and about 0.3 to about 0.6 being even more preferred.

The amount of the trialkylaluminum compound utilized to activate the catalyst of this invention should range from about 0.1 mole to about 10 moles per mole of $V_2O_5$; with 1.0 mole to 5 moles per mole of $V_2O_5$ being preferred. More than 10 moles of the trialkylaluminum may be used, but it provides no additional activation to justify the additional cost. The time required for the activation step may vary from just a few minutes to several hours, such as 5 minutes to 3 hours. It has been found that 15 minutes of activation time produced excellent results.

TYPICAL CATALYST PREPARATION

The catalyst was prepared by impregnation of previously dried gamma alumina, surface area 159 square meters per gram, with an aqueous solution of ammonium metavanadate and ammonium metatungstate. To make these solutions 1.4 g of ammonium metavanadate was added to 25 cc of 70° water. Oxalic acid (caO.9g) was slowly added with stirring until the ammonium metavanadate had dissolved. The pH of the solution was increased by adding 6 drops of concentrated ammonium hydroxide (this step is not necessary, however, since it was included in the procedure described here, it is retained.) To 5 cc of this solution was added 0.0229 g of ammonium metatungstate. After shaking to dissolve the tungsten salt, 2.5 cc of the resulting solution was withdrawn and added to 2.5 cc of the alumina. After two minutes, the slight excess not adsorbed by the $Al_2O_3$ was blotted up. The impregnated $Al_2O_3$ was dried at 170° for 2 hours. Into a tubular stainless steel reactor was placed 1.2 cc of the dried $Al_2O_3$ impregnated with the salts. The reactor was subsequently mounted vertically within a 6 inch cylindrical heater. The catalyst was calcined by blowing air over it at a rate of about 1,000 volumes of air per volume of catalyst per hour at a temperature of 550° C. for 1 hour, followed by cooling to 40° under nitrogen. This resulted in 4.5 percent by weight of $V_2O_5$ and 0.38 percent by weight of $WO_3$ on the alumina. The calcined catalyst was activated by injecting a chlorobenzene solution of trimethylaluminum (two equivalents per equivalent of $V_2O_5$ or 2 moles of $(CH_3)_3Al$ per mole of $V_2O_5$) through a rubber septum arrangement mounted on top of the tubular reactor. Fifteen minutes after the initial contact with the catalyst, the excess trimethylaluminum was dried under vacuum at 50° C. to 70° C.

Catalyst prepared in the manner just described was employed as a metathesis catalyst for propylene. These reactions are described later in this specification.

Utilizing a technique similar to that described above, a variety of other catalysts species can be prepared utilizing different amounts of the vanadium salts and different amounts of the tungsten salts as well as other vanadium salts and other tungsten salts. Other suitable supports which are described elsewhere in this specification may also be used. Also, the catalyst may be activated with other organoaluminum compounds in various amounts as described elsewhere in this specification.

PREPARATION OF BUTENES

In this example, the catalyst employed was prepared in a manner similar to that previously described. In a stainless steel reactor having ¼ inch outside diameter was placed 1.2 cc of the catalyst. This reactor was charged for five minutes with a nitrogen steam. Propylene was passed into the reactor at a rate of 3.2 cc per minute, or GHSV of 160. The reactor was heated to a temperature of 160° C. when the propylene was on stream. The effluent from the reactor was sampled directly into a gas chromatographic column for analysis.

| Catalyst | 4.5% $V_2O_5$; 0.38% $WO_3$ |
|---|---|
|  | 2 moles aluminum trimethyl per mole $V_2O_5$ |
|  | alumina |
|  | Temperature: 160° C. |
| Effluent analysis | 1.6% ethylene |
|  | 42.0% propylene |
|  | 38.7% butenes |
|  | 6.5% pentenes |
|  | 8.6% hexenes |
|  | 1.3% heavier than $C_6$ |

It can be observed that the catalyst of this invention when activated with aluminum trialkyl compounds, i.e., aluminum trimethyl, tend to promote the olefin metathesis reaction and produce butenes from propylene.

While certain representative embodiments and details have been shown for the purpose of illustrating the invention, it will be apparent to those having skill in this art that various modifications and changes can be made therein without departing from the spirit or scope of the invention.

What is claimed is:

1. A method of preparing butenes from propylene which comprises contacting propylene with a catalyst comprising from 3 to 10 percent by weight of $V_2O_5$ and from 0.1 to 3.0 percent by weight of $WO_3$ impregnated on a support which has a surface area of 10 to 400 square meters per gram and which is selected from the group consisting of alumina, silica, thoria, zirconia, oxides of titanium, oxides of magnesium and mixtures thereof, which catalyst has been activated by contact with from 0.1 to 10 moles of a trialkylaluminum selected from the the group consisting of aluminum trimethyl, aluminum triethyl, aluminum tripropyl and aluminum triisobutyl per mole of $V_2O_5$, in which the temperature ranges from about 20 to about 450° C. and the propylene is fed at a GHSV of from about 10 to about 1000.

2. The method according to claim 1 wherein the support is alumina.

3. The method according to claim 1 wherein the support is silica.

4. The catalyst according to claim 1 wherein the organoaluminum compound is aluminum trimethyl.

5. The method according to claim 4 in which the $V_2O_5$ is from 3 to 10 percent by weight and the $WO_3$ is from 0.1 to 3.0 percent by weight and the support is alumina.

* * * * *